United States Patent [19]

Fiume et al.

[11] Patent Number: 5,594,110
[45] Date of Patent: Jan. 14, 1997

[54] PROCESS OF CONJUGATION OF ANTIVIRAL NUCLEOSIDES WITH LACTOSAMINATED HUMAN ALBUMIN

[75] Inventors: Luigi Fiume; Corrado Busi; Giuseppina D. Stefano; Alessandro Mattioli, all of Bologna, Italy

[73] Assignee: Laboratori Baldacci SpA, Pisa, Italy

[21] Appl. No.: 256,415
[22] PCT Filed: Nov. 20, 1993
[86] PCT No.: PCT/EP93/03261
  § 371 Date: Sep. 30, 1994
  § 102(e) Date: Sep. 30, 1994
[87] PCT Pub. No.: WO94/12218
  PCT Pub. Date: Jun. 9, 1994

[30] Foreign Application Priority Data

Nov. 23, 1992 [IT] Italy .................. MI92A2673

[51] Int. Cl.⁶ .............. C07K 1/00; A61K 38/16
[52] U.S. Cl. .......... 530/362; 530/352; 530/358; 530/363; 530/395
[58] Field of Search .................. 530/362, 363, 530/352, 358, 395

[56] References Cited

U.S. PATENT DOCUMENTS 4,725,672 2/1988 Baldacci et al. .................. 530/363
4,794,170 12/1988 Fiume et al. ..................... 530/363

FOREIGN PATENT DOCUMENTS 0184838 6/1986 European Pat. Off. ..

OTHER PUBLICATIONS

Fiume et al, *Pharm. Acta. Helv.*, vol. 63, No. 4–5, pp. 137–139, 1988.
Pharm. Acta Helv,63(4) 137–139 (1988)L. Fiume et al. "Conjugates Of 9–β–D–Arabinofuranosyladenine 5'–Monophosphate".
Analytic Biochemistry, 212(2) 407–411 L. Fuime et al. "Coupling of Antiviral Nucleoside . . . " (1993).
Computational Aspects, A. Polichetti et al. pp. 421–425 (1991) "Improvements In Resolution . . . ".
Database Biosis, A. Polichetti et al. "Prony–householder . . . " (1991).

*Primary Examiner*—Elizabeth C. Weimar
*Assistant Examiner*—Abdel A. Mohamed
*Attorney, Agent, or Firm*—Michael N. Meller

[57] ABSTRACT

A conjugate of an antiviral nucleoside with a lactosaminated human albumin (L-HSA) and its method of preparation is described. The method of preparation involves the reaction of an antiviral phosphorylated nucleoside in the form of an imidizolide with L-HSA at a pH above 7.5 and running the reaction until the desired molar ratio of drug to L-HSA is obtained.

6 Claims, 6 Drawing Sheets

PROCESS OF CONJUGATION OF ANTIVIRAL NUCLEOSIDES WITH LACTOSAMINATED HUMAN ALBUMIN

FIELD OF THE INVENTION

The present invention refers to the preparation of conjugates of antiviral nucleosides and, more particularly to a conjugation process of phosphoric esters of antiviral nucleosides with lactosaminated human albumin.

ART RELATED TO THE INVENTION

It is known, that, to reduce the side effects of antiviral nucleosides in the treatment of chronic hepatitis B, two of these drugs, namely arabinoside adeninc (ara-A) and Acyclovir (ACV), have been conjugated with lactosaminated human albumin (L-HSA) (Fiume L, Bassi B., Busi C., Mattioli A. and Spinosa G., Drug targeting in antiviral chemotherapy. A chemically stable conjugate of 9-β-D-arabinofuranosyl-adenine 5'-monophosphate with lactosaminated albumin accomplishes a selective delivery of the drug to liver cells, Biochem. Pharmacol., 35, 967, 1986;

Fiume L., Bassi B., Busi C., Mattioli A., Spinosa G. and Faulstich H., Galactosylated poly (L-lysine) as a hepatotropic carrier of 9-β-D-arabinofuranosyladenine 5'-monophosphate, FEBS Letters, 203, 203, 1986).

L-HSA is a neoglycoprotein which penetrates selectively into the hepatic cells (Wilson G., Effect of reductive lactosamination on the hepatic uptake of bovine pancreatic ribonuclease A dimer, J. Biol. Chem., 253, 2070, 1978) where it is digested in the lysosomes (Ashwell G. and Harford J., Carbohydrate specific receptors of the liver Ann. Rev. Biochem, 51, 531, 1982).

Experiments conducted in mice with hepatitis caused by the virus of ectromelia have shown that the conjugates with the ara-A and with the ACV penetrate selectively in the liver where they release the drugs in an active form. In patients with cronic hepatitis induced by virus B, the ara-A bound to the L-HSA inhibited the viral replication at a dose 3–6 times lower than that of the free antiviral drug. (Fiume L., Torrani Cerenzia M. R., Bonino F., Busi C., Mattioli A., Brunetto M. R., Chiaberge E. and Verme G., Inhibition of hepatitis B virus replication by vidarabine monophosphate conjugated with lactosaminated serum albumin, Lancet, ii, 13, 1988). In order to bind the ara-A and the ACV with the L-HSA, these compounds have been phosphorilated at the OH primary group according to Yoshikawa's et al. method (Yoshikawa M., Kato T. and Takenishi T., A novel method for phosphorylation of nucleosides to 5'-nucleotides, Tetrahedron Lett. 50, 5065, 1967); the phosphorilated compounds have been further conjugated with the L-HSA with the use of 1-ethyl-3-(dimethylaminopropyl) carbodiimide (ECDI), adjusting the pH of the reaction medium to 7.5 before adding ECDI and prolonging the reaction for 24 hours at the temperature of 25° C. (Biochem. Pharmacol. 35, 967, 1986; Fiume L., Bassi B., Busi C. and Mattioli A., Preparation of lactosaminated albumin-ara-AMP conjugate which remains soluble after lyophilization, Pharm. Acta Helv., 60, 318, 1985). The L-HSA-ara-AMP conjugates so obtained have molar ratios (MR) drug/L-HSA from 10 to 14. In these conjugates, both ara-A monophosphate (ara-AMP) and ACV monophosphate (ACVMP) are bound to L-HSA by means of phosphoamide bonds with lysine and histidine residues (Fiume L., Bassi B. and Bongini A., Conjugates of 9-β-D-arabonofuranosyladenine 5'-monophosphate (ara-AMP) with lactosaminated albumin. Characterization of the drug-carrier bonds, Pharm. Acta Helv., 63, 137, 1988; Fiume L., Busi C., Mattioli A., Spinelli C. and Spinosa G., A conjugate of acyclovir monophosphate with lactosaminated albumin releases the phosphorylated drug in liver cells, Naturwissenschaften, 76, 74, 1989).

The conjugation with carbodiimides has the disadvantage of giving place to side reactions.

It causes a polymerisation of the L-HSA molecules that increases the potential immunogenicity of the conjugate.

The polymers originate from the formation (performed by the carbodiimide) of carboamide bonds linking the protein molecules (Sheehan J. C. and Hlavka J. J., The cross-linking of gelatin using a water-soluble carbodiimide, J. Am. Chem. Soc., 79, 4528, 1957).

Furthermore, by using ECDI, some carboxylic groups are definitively modified, probably because of the formation of a stable N-acylurea (Riehm J. P. and Scheraga H. A., Structural studies of ribonuclease. XXI. The reaction between ribonuclease and a water-soluble carbodiimide, Biochemistry, 5, 99, 1966).

Endeavours have been made to eliminated these side reactions by making the conjugation to occur in two steps, as suggested by Humayun and Jacob (Humayun M. Z. and Jacob T. W., Immunologic studies on nucleid acids and their components I. An analysis of the specificity of anti-deoxyadenylate antibodies by a membrane-binding technique, Biochim; biophys. Acta, 331, 41, 1973), and by Davis Preston (Davis M. B. and Preston J. F., A simple modified carboiimide method for conjugation of small molecolar weight compounds to immunoglobulin G with minimal protein crosslinking. Analyt. Biochem., 116, 402, 1981) for the conjugation of other compounds with proteins. The ara-AMP was first reacted with ECDI alone, at different pH and temperature conditions and, thereafter, after varying times, the reaction mixture has been added to the L-HSA. All the attempts made, however, failed.

The polymerisation decreased but was not eliminated and the ara-AMP/L-HSA molar ratios (MR) were never higher than 4.

SUMMARY OF THE INVENTION

It has then been envisaged to conjugate the ara-AMP by activating this compund not with ECDI, but by forming the imidazolide (ara-AMPIm) thereof, of the formula:

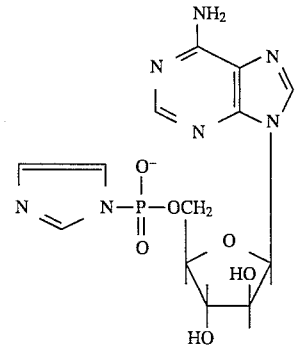

The imidazolides of phosphoric esters are as a matter of fact good phosphorylating agents and react with alcoholic, amino and carboxylic groups, forming phosphoesters, phosphoamidic and phosphoanhydridic groups, respectively (Baddiley J., Buchanan J. G. and Letters R., Phosphorylation through glyoxalines (imidazoles) and its significance in enzymic transphosphorylation, J. Chem. Soc., 2812, 1956; Staab H. A., Schaller H. and Cramer F., Imidazolide der phosphorsaure, Angew Chem., 71, 736, 1959). The conjugation of the ara-AMP with the L-HSA utilizing the imidazolide thereof has been realized by reacting for 24 hours this compound with the L-HSA at 25° C. and at a pH of 7.5 (Polichetti A., Viti V., Barone P., Colonna F. and Fiume L., Prony-Householder method applied to $^{31}p$ NMR signals. II. Study of conjugates of ara-AMP with lactosaminated albumin, Physics in Medicine and Biology, 37, 1, 1992). With this procedure non polymerisation occurred, but the molar ratio drug/L-HSA has never proved to be higher than 6, this value being half of that of the conjugate obtained by using ECDI.

This low molar ration represents a remarkable disadvantage. Indeed, to introduce the amount of coupled ara-AMP needed to inhibit the replication of the virus of B hepatitis (1.5 mg/Kg), a quantity of this conjugate twice as much as that of the conjugate prepared with ECDI (35 mg/Kg, corresponding to 1.5 mg/Kg of ara-AMP), should be administered to patients.

Such a dosage increase should be avoided since the L-HSA-ara-AMP conjugates give rise, already at 175 mg/kg, to a swelling of the lysosomes of the hepatic cells, as a consequence of an incomplete digestion of the protein carrier (Fiume L., Betts C. M., Busi C., Corzani S., Derenzini M., Di Stefano G. and Mattioli A., The pathogenesis of vacuoles produced in rat and mouse liver cells by a conjugate of adenine arabinoside monophosphate with lactosaminated albumin, J. Hepatol., 15, 314, 1992). It therefore appears desirable and is the main object of the present invention to provide a process for the preparation of conjugates of L-HSA with ara-AMP (and with other antiviral phosphorylated nucleosides), in which there are obtained complexes having molar ratios drug/L-HSA at least equal to those of the conjugate prepared with ECDI, without the drawbacks concerning this latter and previously mentioned.

This purpose is achieved with the process of the present invention, of the type wherein an antiviral phosphorylated nucleoside in the form of imidazolide is reacted with L-HSA, the process being characterized in that the reaction takes place at a pH higher than 7.5, prolonging the conjugation reaction until the maximum desired molar ratio drug/L-HSA is obtained, this molar ratio being at least equal to that of the corresponding conjugate prepared with ECDI.

PREFERRED EMBODIMENTS

In the preferred embodiment of the process according to the present invention, the conjugation reaction is carried out at a pH between 8.5 and 9.5, at a temperature higher than 25° C. and for a period of at least 24 hours, and conjugates that, in the case of the ara-AMP, have molar ratios (MR) equal to and prevailingly higher than those prepared with ECDI without polymerisation of the protein and without the other drawbacks associated with the use of ECDI, are obtained.

Figure 1:
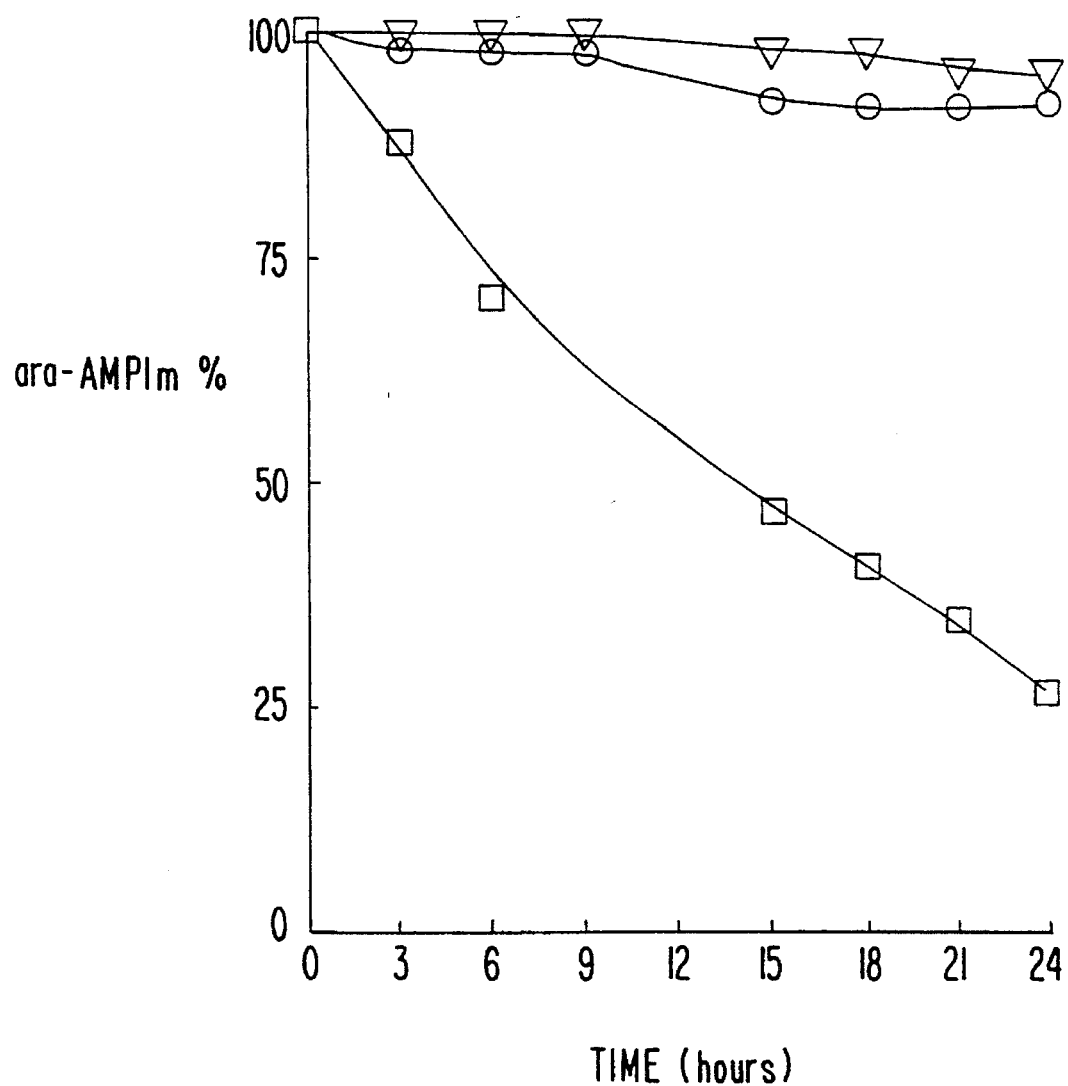
FIGS. 1 and 2 show the ara-AMPIm hydrolyzed percentage, as a function of time, both at 25° C. and 37° C.
Figure 2:
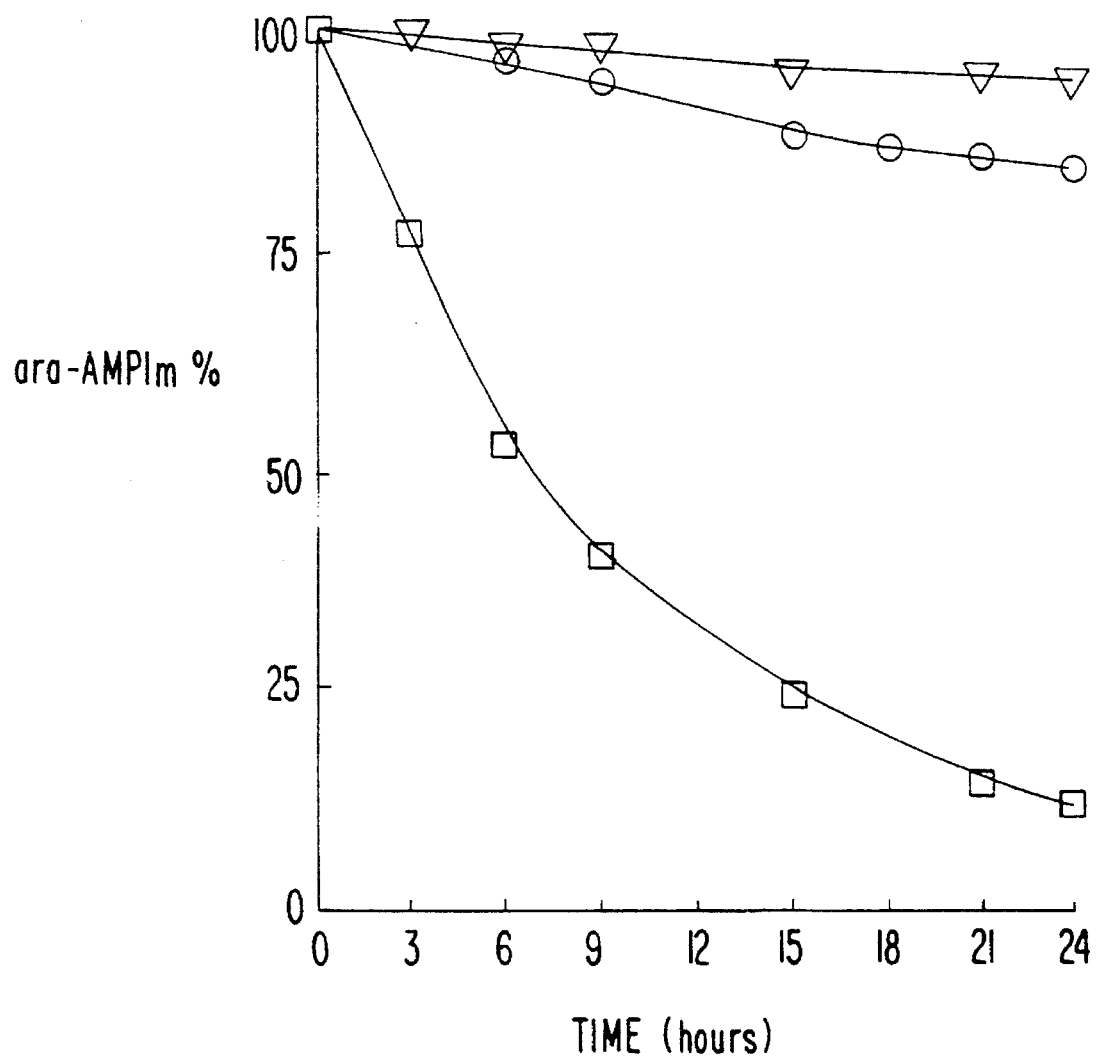

The process of the present invention seems to be surprising for the reason that, whilst the ara-AMPIm at a pH 7.5 is hydrolized (at 37° C. faster than at 25° C.), it has been found that at a pH 8.5 and 9.5 it is pratically stable either at 25° C. or at 37° C. Consequently, by virtue of the stability of the ara-AMPIm at these high pH, the conjugation reaction can be prolonged for more than 24 hours and can be carried out at temperatures higher than 25° C. The FIGS. 1 and 2 show the ara-AMPIm hydrolized percentage, as function of the time, both at 25° C. and 37° C. In the reported experiments in both figures at the ara-AMPIm disappearance corresponds the appearance of an equimolecular quantity of ara-AMP in the HPLC chromatogram.

Figure 3:
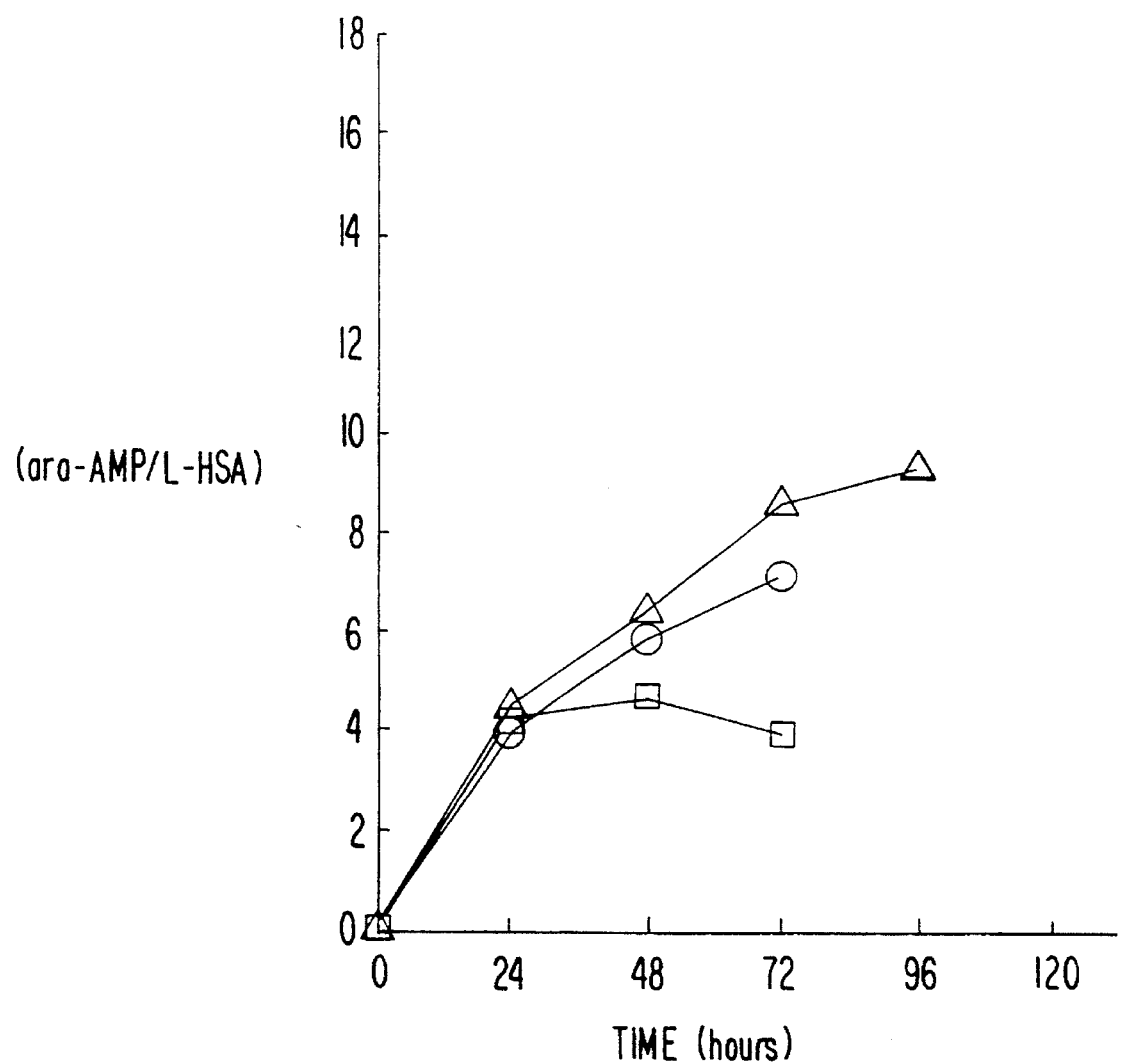
FIGS. 3 and 4 show the molar ratio values of ara-AMP/L-HSA as a function of reaction time at various pH values.
Figure 4:
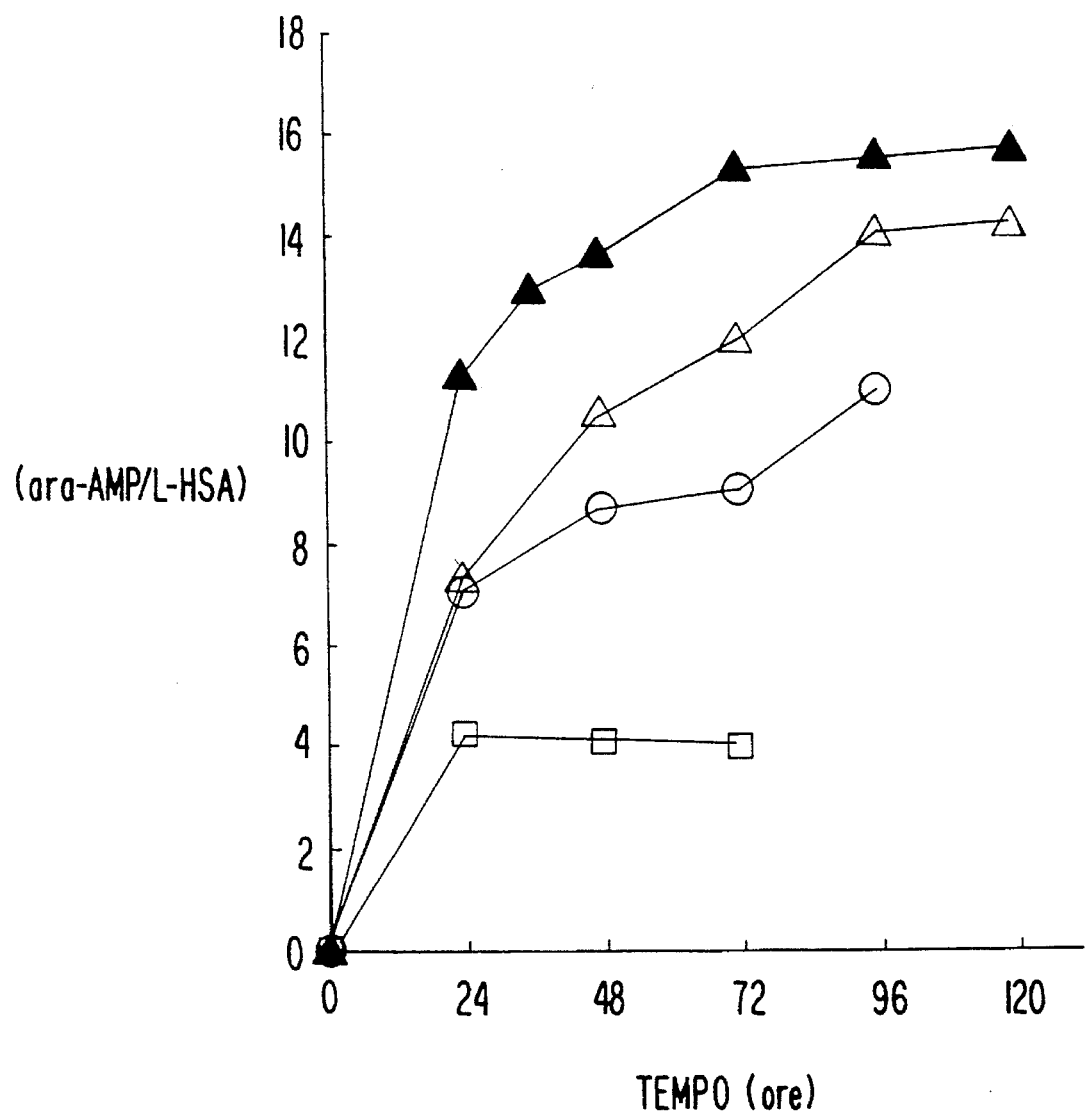

In turn, FIGS. 3 and 4 show the molar ratio values ara-AMP/L-HSA, as function of the reaction time, at different pH values and with the ara-AMPIm concentration of 50 mg/ml and 75 mg/ml, keeping the L-HSA concentration of 50 mg/ml. From these experimental data it is seen that when the conjugation via ara-AMPIm takes place at a pH of 9.5 and at 37° C., molar ratios equal or higher that those prepared with ECDI are achieved.

Table I shows that with the NMR spectrospic analysis of the $^{31}p$, the "chemical shifts" of a conjugate prepared via ara-AMPIm are equal to those of a conjugate obtained with ECDI, as described in Biochemical Pharmacol. 35, 967, 1986. This result proves that, like in the conjugate prepared with ECDI (Fiume et al., Phrma. Acta Helv. 63, 137, 1988) and in those prepared via ara-AMPIm at pH 7.5 (Polichetti et al., Physics in Medicine and Biology 37, 1, 1992), also in the conjugate prepared via ara-AMPIm at a pH higher than 7.5 the drug is bound to the L-HSA by means of phosphoamide bonds with the ε-amino group of lysine residues and with imidazolic nitrogen of histidine residues.

The formation of these bonds indicates that the increase of the molar ratios drug/carrier, achieved by increasing the pH from 7.5 to 8.5 or 9.5 is due, besides to the higher ara-AMPIm stability, also to the larger number of lysine amino groups of the L-HSA which, at the pH values of 8.5–9.5, are not protonated and are therefore capable to bind the ara-AMP.

TABLE 1

| $^{31}P$NMR chemical shifts of the L-HSA-ara-AMP[a] | |
| --- | --- |
| L-HSA-ara-AMP (ECDI) | −8,7; 9,1 |
| L-HSA-ara-AMP (ara-AMPIm)[b] | −8,7; 9,1 |

[a] The "chemical shifts" refer to a 85% $H_3PO_4$ external standard
[b] Reaction conditions: ara-AMPIm 75 mg/ml; L-HSA 50 mg/ml; pH 9.5; 37° C.; 36 hours incubation. MR = 12.5

Unlike the conjugates prepared with ECDI, wherein in the $^{31}P$ NMR spectrum the peaks of the bonds with histidine and lysine are practically the same, in the conjugate prepared via ara-AMPIm the peak corresponding to the bond with the lysine is 2–3 times as high as that corresponding to the bond with histidine.

Figure 5A:
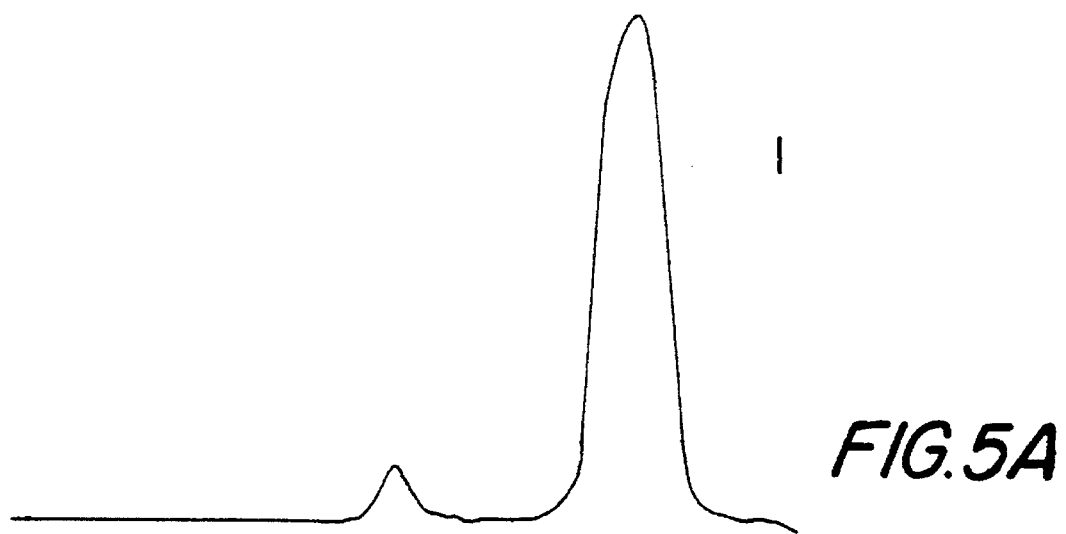
FIG. 5 shows the SDS-Gel electrophoresis of two L-HSA-ara-AMP conjugates.
Figure 5B:
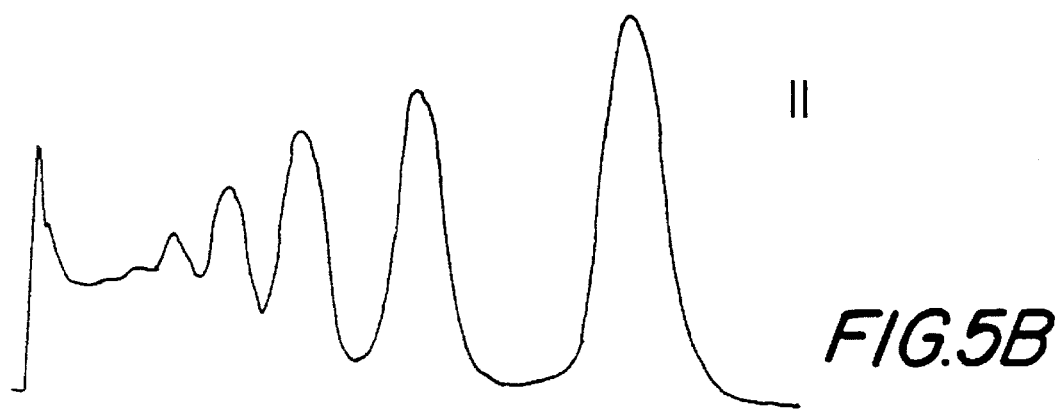
Figure 5C:
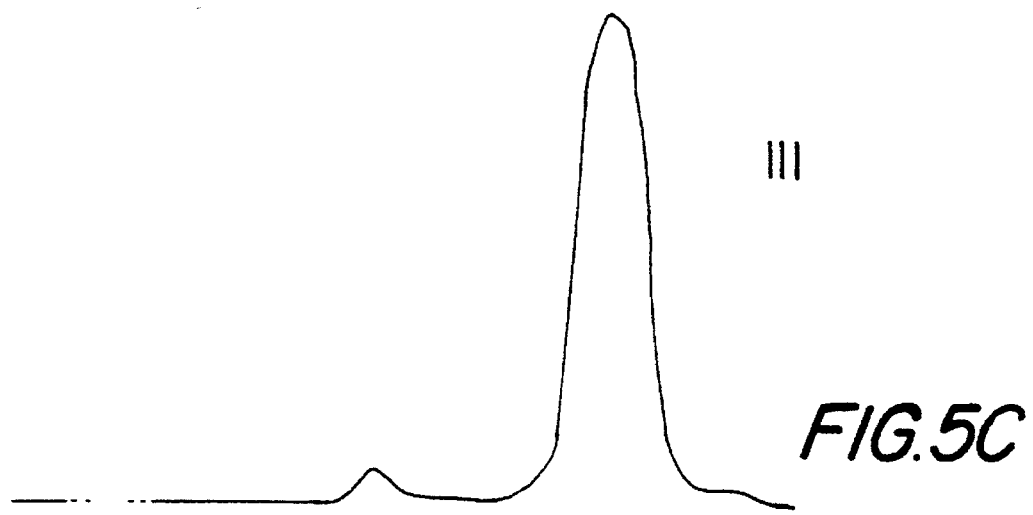

FIG. 5 illustrates the SDS-Gel electrophoresis of two L-HSA-ara-AMP conjugates, of which one prepared with the use of ECDI and the other obtained by the imidazolide of the ara-AMP. As it can be seen in the figure, the via ara-AMPIm conjugation did not cause any polymerisation of the protein.

So far FIG. 5 is concerned, it must be noted that the conjugate (II) was prepared with the use of ECDI, as described in the already cited Work published on Biochem. Pharmacol, 35, 967, 1986, whereas the other conjugate (III) has been prepared by means of ara-AMPIm. The molar ratio (MR), of the conjugate made with ECDI was 10; the conjugation conditions via ara-AMPIm were those already mentioned in the paragraph (b) of Table 1, except that the incubation period was of 24 hours and the MR was 11.

The determination of the isoelectric points of the HSA, L-HSA and of L-HSA-ara-AMP conjugates prepared either via ara-AMPIm at pH 8.5–9.5 or using ECDI has pointed out that the utilization of the imidazolide eliminates also the other side reaction produced by the carbodiimide, consisting in the elimination of some carboxylic groups of the protein due to the probable formation of stable N-acylureas (see the pages already cited and published on Biochemistry 5, 99, 1966).

The isoelectric points both of HSA and L-HSA resulted to be in the range of 4.5–5.5.

The conjugation with ara-AMP should lower these values due to the negative charge of the phosphate introduced in the L-HSA.

This occurs for the conjugate prepared via ara-AMPIm (conjugation conditions equal to those described in Table 1). The pI values of this conjugate resulted to be 4.3–4.5. But for the conjugate prepared with ECDI the isoelectric precipitation occurred at pH higher than those of the HSA and L-HSA. This result can be easily explained by the N-acylureas formation that suppress the negative charge of the L-HSA carboxylilc groups and introduce the positive charge of the ECDI side chain. In conclusion, the conjugation via ara-AMPIm at pH 9.5 and 37° C. allows to obtain conjugates with MR equal to or higher than those prepared with the use of the ECDI, avoiding on the other hand the side-reactions produced by the use of the carbodiimides (protein polymerisation and elimination of carboxylic groups probably because of N-acyl ureas formation).

Three other antiviral nucleosidic compounds, namely ACV, dideoxycytidine (DDC) and azidothymidine (AZT), have been phosphorylated according to the already cited Yoshikawa et al. method, and conjugated to the L-HSA according to the present invention, via the respective imidazolides, at pH 9.5 and at 37° C.

Figure 6:
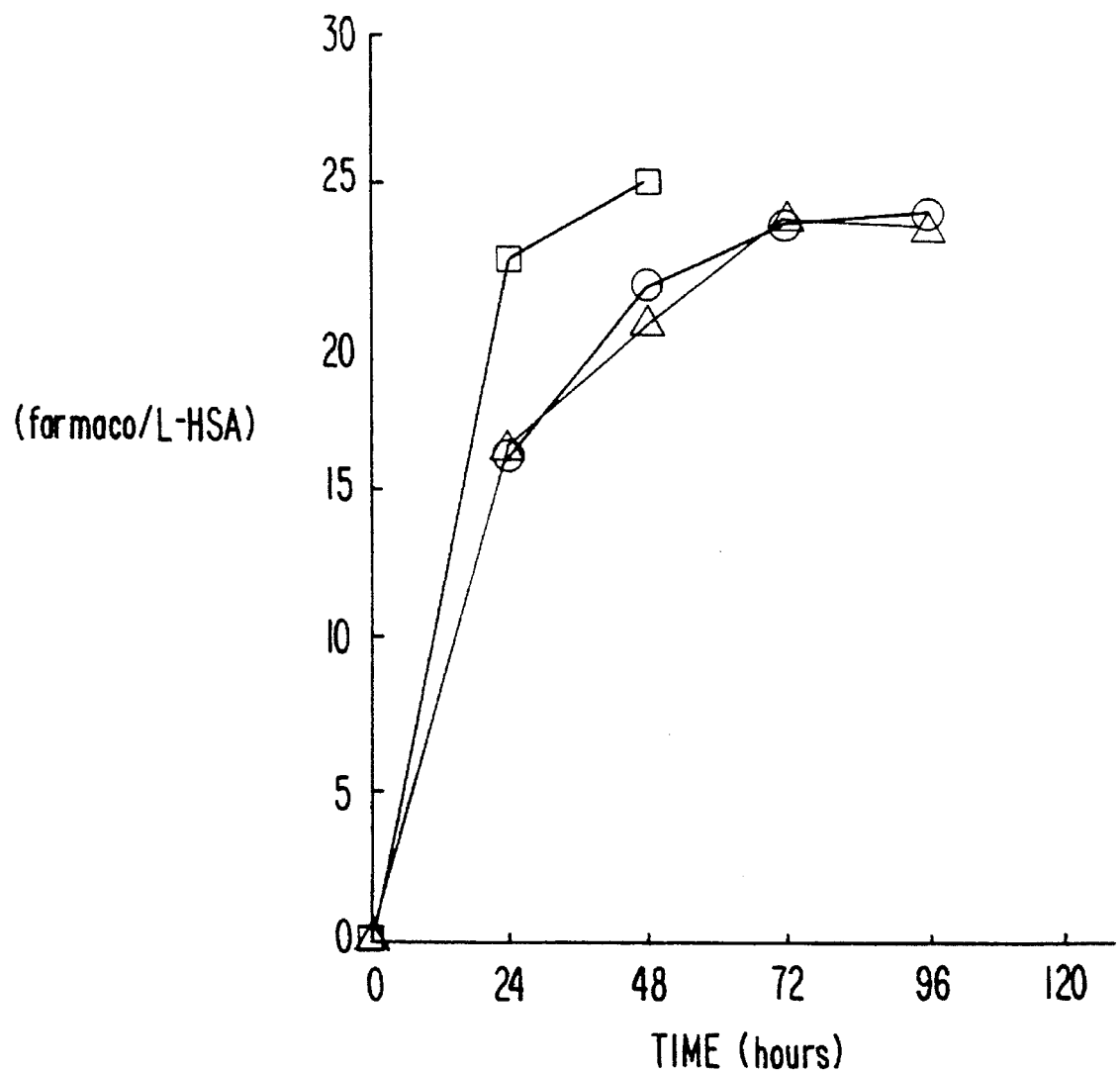
FIG. 6 shows the values of the respective molar ratios (MR) of the obtained conjugates.

In FIG. 6 are reported the values of the respective molar ratios (MR) of the obtained conjugates; the imidazolides of these compounds have been obtained and isolated with the procedure used for preparing the ara-AMPIm, the L-HSA concentration was of 50 mg/ml whilst that of DDCMPIm, ACVMPIm and AZTMPIm was of 75 mg/ml.

The following example illustrates the experimental procedure adopted for the preparation of the conjugate according to the present invention. This is obviously an illustrative example not to be absolutely considered as limiting.

The ara-AMP imidazolide has been prepared with the Lohrmann and Orgel method (Lohrmann R. and Orgel L. E. Preferential formation of (2'–5') linked internucleotide bonds in non-enzymatic reaction, Tetrahedron, 34, 853, 1978). The experiments of hydrolysis of the ara-AMPIm and of conjugation with the L-HSA made at pH 7.5 have been conducted in a non buffered aqueous solution adjusting the pH at 7.5 with NaOH immediately after the dissolution of the ara-AMPIm.

After 24 hours incubation, the pH was 6.6 and 6.2 in the hydrolysis experiments at 25° C. and at 37° C. respectively, and 7.0 in the conjugation experiments at 37° C. The experiments carried out at pH 8.5 and 9.5 have been conducted using a 0.2M boric acid-borax buffer (pH 8.5) and a 0.1M sodium carbonate-bicarbonate buffer (pH 9.5), respectively. The figures show the ara-AMPIm and L-HSA concentrations. At the times indicated in the figures, the conjugates have been dialyzed in cold room against 0.9% NaCl or diafiltered on PM 10 (Amicon) membranes. The MR have been spectrofotometrically determined as indicated in Biochem. Pharmacol, 35, 967, 1986. In the hydrolysis experiments, the ara-AMPIm and ara-AMP concentrations were measured by HPLC using a Bondapack C18 column and eluting as disclosed in Mc Cann W. P., Hall L. M., Siler W. Barton N. and Whitley R. J., High-pressure liquid chromatographic methods for determining arabinosyladenine-5'-monophosphate, arabinosyladenine, and arabinosylhypoxanthine in plasma and urine, Antimicrob. Agents Chemoter., 28 265, 1985.

From the foregoing description it is evident that with the process of the present invention, conjugates not only free from the undesirable chemical changes of the L-HSA carrier, such as those previously described, are obtained, but also and above all L-HSA conjugates of antiviral drugs capable of being selectively carried into the target organ, allowing the administration of lower doses of conjugate with the same therapeutic effect or the increasing of the therapeutic effect with the same dosage of the conjugated compound.

It also appears that, as regards the preparation of the imidazolides of the antiviral phosphorylated nucleosides, alternative routes are possible and predictable, this without having consequences whatsoever on the process of the invention and on the resulting conjugated.

We claim:

1. A process for the preparation of conjugates of antiviral nucleosides with lactosaminated human albumin (L-HSA) in which an antiviral phosphorylated nucleoside in the form of an imidazolide is reacted with L-HSA, wherein the reaction is carried out at a pH higher than 7.5 and at a temperature above 25° C., and prolonging the conjugation reaction until the desired molar ratio of drug:L-HSA is obtained.

2. The process according to claim 1, wherein said antiviral nucleoside is selected from the group consisting of arabinoside adeninc acyclovir, dideoxicytidine and azidothydine.

3. The process according to claim 1, wherein the reaction is carried out at a temperature of about 42° C. and at a pH of about 10.

4. The process according to claim 1, in which said reaction is carried out at a pH between 8.5 and 9.5.

5. The process according to claim 4, in which the conjugation reaction is carried out at 37° C. in more than 24 hours.

6. The process according to claim 5, in which said reaction takes place in 36 hours.

* * * * *